United States Patent
Liao et al.

(10) Patent No.: US 7,086,919 B2
(45) Date of Patent: Aug. 8, 2006

(54) DETECTION AND REPAIR SYSTEM AND METHOD THEREOF

(75) Inventors: Meng-Chieh Liao, Hsinchu (TW); Jiun-Haw Lee, Taipei (TW); Chi-Chung Chen, Taipei (TW)

(73) Assignee: RiTdisplay Corporation, Hsinchu (TW)

( * ) Notice: Subject to any disclaimer, the term of this patent is extended or adjusted under 35 U.S.C. 154(b) by 317 days.

(21) Appl. No.: 10/442,054

(22) Filed: May 21, 2003

(65) Prior Publication Data

US 2004/0082252 A1 Apr. 29, 2004

(30) Foreign Application Priority Data

Oct. 25, 2002 (TW) ................. 91125339 A

(51) Int. Cl.
*H01J 9/00* (2006.01)
*H01J 9/50* (2006.01)
*H01J 9/44* (2006.01)
*H01T 21/00* (2006.01)
*F23Q 23/08* (2006.01)

(52) U.S. Cl. ............... 445/64; 445/2; 445/3; 445/4; 445/61; 445/63

(58) Field of Classification Search ............ 445/61, 445/64, 2, 3
See application file for complete search history.

(56) References Cited

U.S. PATENT DOCUMENTS

| | | | |
|---|---|---|---|
| 6,729,922 B1 * | 5/2004 | Hiroki | 445/3 |
| 6,888,519 B1 * | 5/2005 | Yamano et al. | 345/75.2 |
| 6,909,111 B1 * | 6/2005 | Yamagata et al. | 257/59 |

* cited by examiner

*Primary Examiner*—Nimeshkumar D. Patel
*Assistant Examiner*—Elizabeth Rielley
(74) *Attorney, Agent, or Firm*—Jiang Chyun IP Office

(57) ABSTRACT

A detection and repair system includes an optical microscope, an image-retrieving device, an emission detector, a data controller, and a laser beam generator. When detecting the location of a defect, the system charges a detected region of an organic electroluminescent device with a negative bias or low forward bias before the device is lighted on. Then, the emission detector detects the locations of defects, which generate emission such as photons, thermal or IR emission, in an enlarged image. The laser beam generator generates a laser beam, which is used to isolate one of the defects. Furthermore, this invention also discloses a method for detecting and repairing an organic electroluminescent device.

15 Claims, 4 Drawing Sheets

DETECTION AND REPAIR SYSTEM AND METHOD THEREOF

This nonprovisional application claims priority under 35 U.S.C. § 119(a) on Patent Application No. 091125339 filed in TAIWAN on Oct. 25, 2002, which is(are) herein incorporated by reference.

BACKGROUND OF THE INVENTION

1. Field of Invention

The invention relates to a detection and repair system and method thereof, and in particular, to a system and method, of detecting an organic electroluminescent device and repairing defects of the organic electroluminescent device.

2. Related Art

Information communication technology and portable communication display products in particular have become a major focus of industry. Flat panel displays provide an interface between humans and information, thus they have become a product of key interest to users and manufacturers alike. Present examples of flat panel displays include plasma display panels, liquid crystal displays (LCDs), inorganic electroluminescence displays, light-emitting diode (LED) displays, vacuum fluorescence displays, field emission displays, and electro-chromic displays among others.

Compared to other flat panel displays, organic electroluminescent devices, such as organic electroluminescent panels or organic electroluminescent components, are self-emissive, and possess the advantages of full viewing angle, high power efficiency, easy manufacture, low cost, rapid response, and full color. Therefore, organic electroluminescent devices may become the major choice for flat panel display technology in the future.

Those skilled in the art should know that organic electroluminescent devices utilize the self-emissive properties of certain functional materials to achieve the objective of displaying. An organic electroluminescent device consists of a pair of electrodes and an organic functional material layer. When applying the voltage to the electrodes, the electrons and holes move and recombine in the organic functional material layer to generate excitons. The organic functional material layer can then radiate light of different colors according to their characteristics.

If particles exist on a pixel of the organic electroluminescent device during manufacture of the organic electroluminescent device, the multiple layers of the pixel may not be stacked successfully. Additionally, the electrodes of the organic electroluminescent device may contact each other and short-circuit. Consequently, the luminance of the organic electroluminescent device decreases, and the quality and reliability of the organic electroluminescent device decreases. Thus, it is critical to detect and repair the products to ensure the quality thereof.

To solve the mentioned problem, those skilled in the art usually utilize a detection machine with an optical microscope and a repairing machine having a laser beam generator to detect and repair an organic electroluminescent device, respectively.

In the conventional detection process, a detection machine scans an organic electroluminescent device to determine whether the pixel of the organic electroluminescent device has a defect or not, and then positions the location of the defect. In a subsequent step, the defective organic electroluminescent device is transported to the repairing machine to perform a repairing process. In such a case, the defect is radiated with the laser generated by the laser beam generator, thus isolating the defect.

In view of the previously mentioned detection and repairing processes, it is necessary to transport the organic electroluminescent device from the detection machine to the repairing machine as defects are detected. In practice, because the organic electroluminescent device is transported from the detection machine to the repairing machine, the detected defect of the organic electroluminescent device cannot be repaired directly. As with the prior process, the organic electroluminescent device is scanned again in order to locate and then repair the defect.

As mentioned above, a foreign particle exists on the pixel may induce the stacking problem, and further induce a short circuit. However, if the particle is smaller than a certain size and the short-circuited issue does not occur, the defect caused by this particle can be ignored, and it is unnecessary to repair this defect. In the conventional detection process, the defect is detected with the optical microscope by way of scanning. However, this method cannot determine whether the defect will cause the short-circuited issue or not, and as a result, all detected defects will be repaired during the repairing process. Consequently, the conventional technology will scan an organic electroluminescent device, locate defects, scan the device again, locate the defects again, and then repair all the detected defects, resulting in wasting time and resources in the manufacturing processes.

Thus, it is an important objective of the invention to efficiently detect and repair defects of an organic electroluminescent device.

SUMMARY OF THE INVENTION

In view of the above-mentioned problems, an objective of the invention is to provide a detection and repair system and method thereof, which can efficiently detect and repair an organic electroluminescent device.

The invention is characterized in that a detected region of an organic electroluminescent device is charged with a negative bias or a low forward bias before the device is lighted on, a emission detector (ex. photon, thermal or IR emission detector) is used to detect the location of a defect, which radiates photons, thermal or IR emission, in an enlarged image, and a laser beam generator is used to generate a laser beam to isolate the defect.

To achieve the above-mentioned objectives, a detection and repair system of the invention includes an optical microscope, an image-retrieving device, an emission detector, a data controller, and a laser beam generator. The optical microscope enlarges an image of a detected region located on an organic electroluminescent device. The image-retrieving device retrieves the enlarged image, and the emission detector detects a location of a defect, which generates emission such as photons, thermal or IR emission, from the enlarged image. The data controller stores the image and the location of the defect, and generates a first control signal according to the image and the location of the defect. The laser beam generator generates a laser beam for isolating the defect according to the first control signal. The laser beam goes through the optical microscope that can focus on the laser beam to the location of the defect.

Furthermore, the invention also discloses a detection and repairing method, which includes the following steps of: using an optical microscope to enlarge an image of a detected region located on an optical electroluminescent device; using an image-retrieving device to retrieve the enlarged image; charging the detected region with a negative bias or a lower forward bias before the device is lighted on, and use an emission detector to detect a location of a defect generating emission, such as photons, thermal or IR emission, in the enlarged image; using a data controller to store the enlarged image and the location of the defect, and generating a first control signal according to the enlarged image and the location of the defect; and using a laser beam generator to generate a laser beam for isolating the defect according to the first control signal.

As mentioned above, since the detection and repair system and method thereof of the invention charge the detected region of the organic electroluminescent device with a negative bias or a low forward bias before the device is lighted on, utilize the photon thermal or IR emission detector to detect the location of the defect emitting photons, thermal or IR emission and utilize the laser beam generator to generate the laser beam for isolating the defect, it is unnecessary to apply a conventional detection machine and a conventional repairing machine to perform detecting and repairing processes. Thus, the defects of an organic electroluminescent device can be detected and repaired efficiently.

BRIEF DESCRIPTION OF THE DRAWINGS

The invention will become more fully understood from the detailed description given in the herein below illustration, and thus are not limitative of the present invention, and wherein.

DETAILED DESCRIPTION OF THE INVENTION

The detection and repair system according to a preferred embodiment of the invention will be described hereinbelow with reference to the accompanying drawings, wherein the same reference numbers refer to the same elements. It should be noted that the organic electroluminescent devices described in the following include organic electroluminescent panels and organic electroluminescent components.

Figure 1:
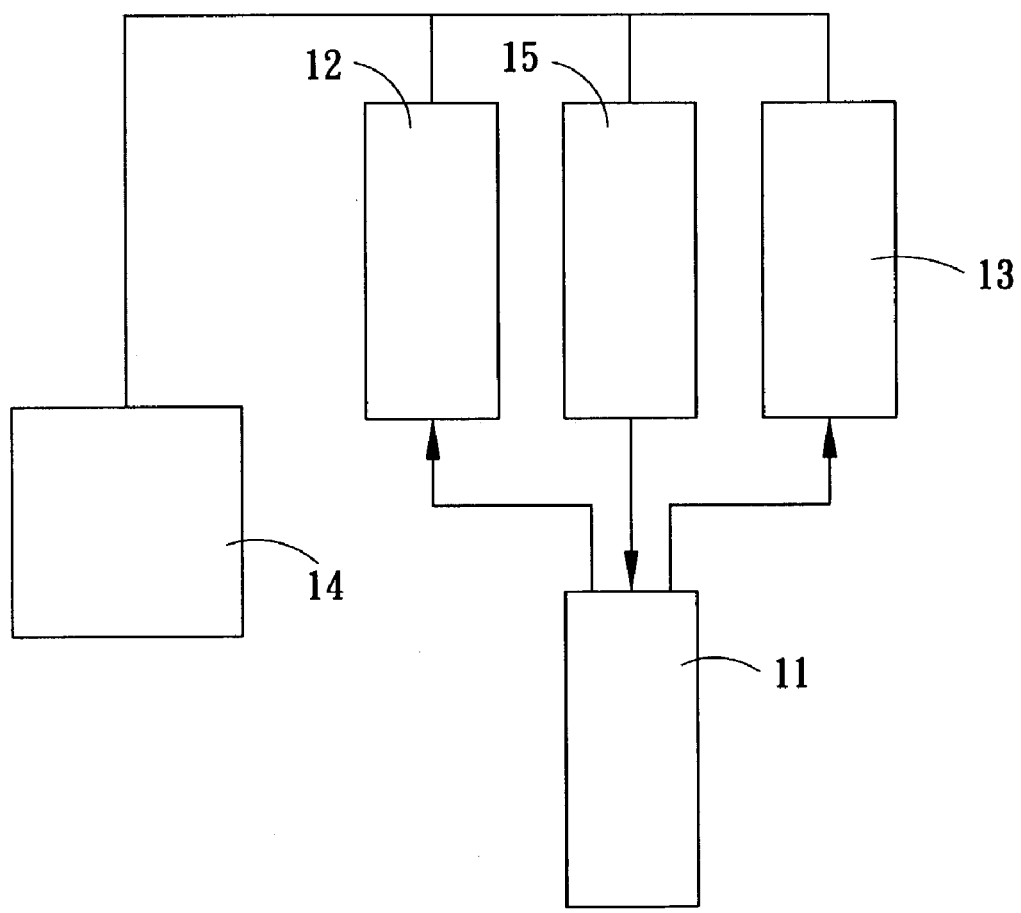
FIG. 1 is a block diagram showing a detection and repair system of the invention.

With reference to FIG. 1, a detection and repair system 1 according to a preferred embodiment of the invention includes an optical microscope 11, an image-retrieving device 12, an emission detector 13, a data controller 14, and a laser beam generator 15.

Figure 2:
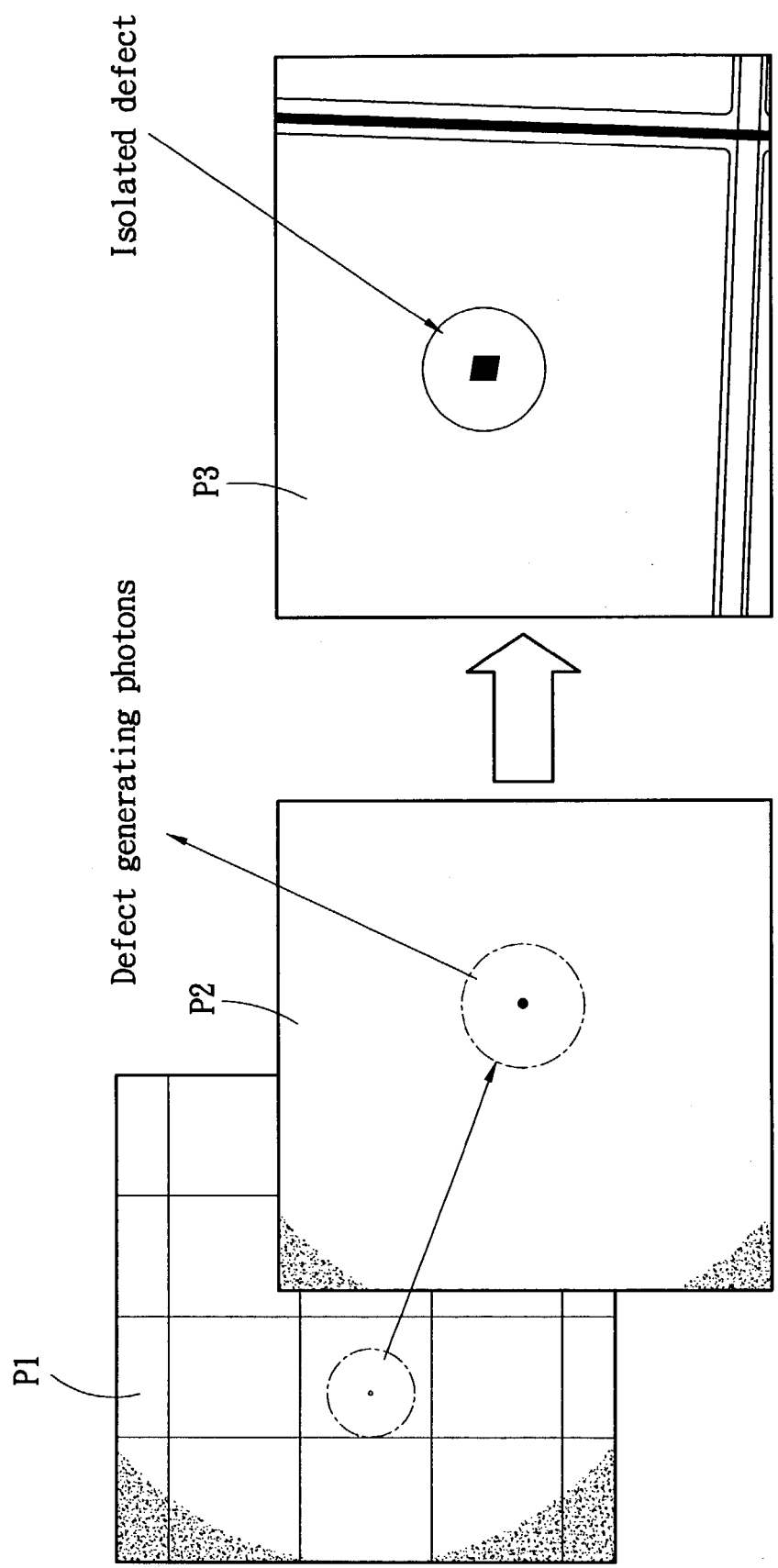
FIG. 2 is a schematic illustration showing a specific pixel when using a detection and repair system of the invention to detect and repair the same.
Figure 3:
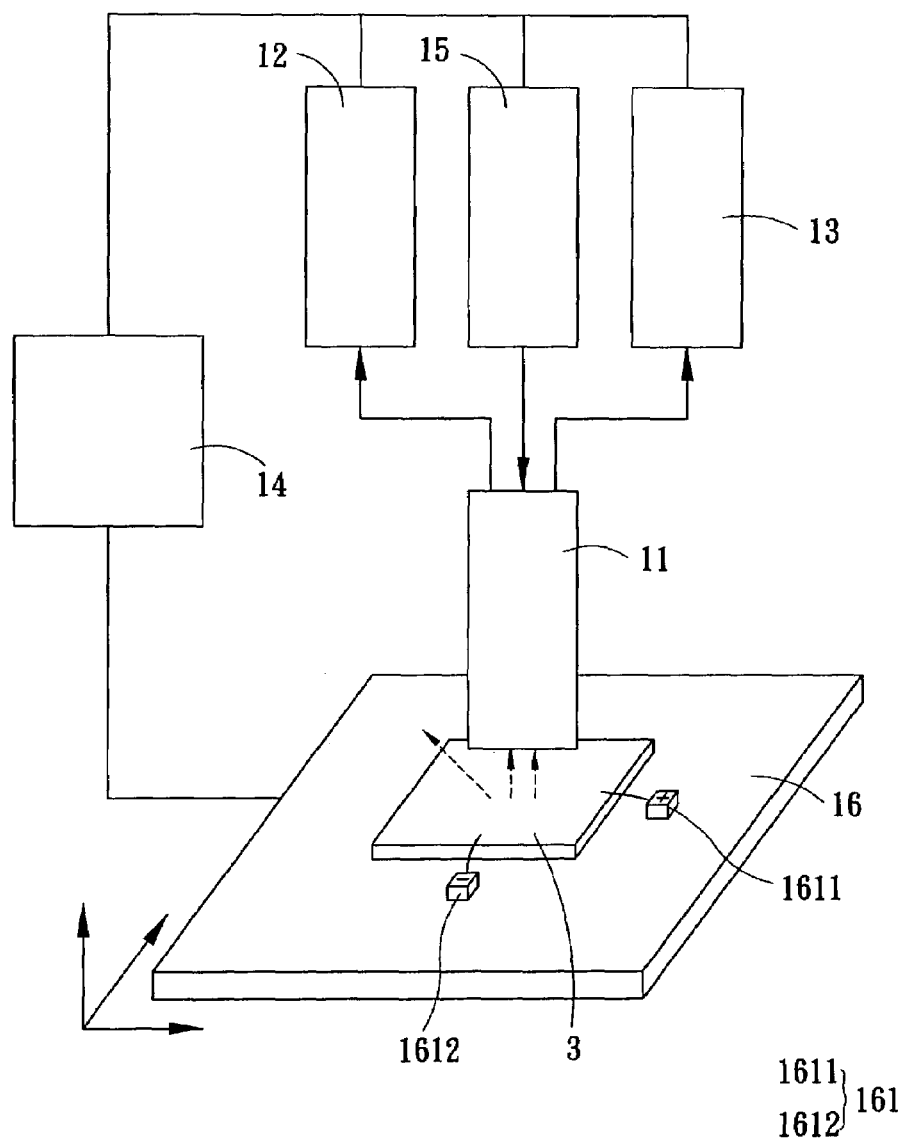
FIG. 3 is a schematic illustration showing a structure of a detection and repair system of the invention.

The optical microscope 11, as shown in FIG. 3, is used to enlarge an image of a detected region in an organic electroluminescent device 3. The image-retrieving device 12 connects to the optical microscope 11 and retrieves the enlarged image P1 shown in FIG. 2. In the present embodiment, the image-retrieving device 12 is a CCD camera.

The emission detector 13, such as a photon, thermal or IR emission detector, connects to the optical microscope 11 and detects a location of a defect, which emits emission, such as photons, thermal or IR emission, as the reference number P2 shown in FIG. 2, in the enlarged image. The data controller 14 electrically connects to the image-retrieving device 12 and the emission detector 13, respectively. The data controller 14 can store the enlarged image retrieved by the image-retrieving device 12 and the location of the defect detected by the emission detector 13. Then, the data controller 14 generates a first control signal according to the enlarged image and the location of the defect. In the embodiment, the data controller 14 is a computer.

The laser beam generator 15 electrically connects to the data controller 14 and connects to the optical microscope 11. The laser beam generator 15 generates a laser beam, which goes through the optical microscope 11 that can focus on the laser beam to the location of the defect, for isolating the defect. The optical microscope 11 can be a specific lens that can focus on the laser beam to the location of the defect. Accordingly, the defect located in the detected region of the organic electroluminescent device 3 can be repaired. The image of reference number P3 shown in FIG. 2 illustrates the repaired defect.

In addition, the detection and repair system 1 further includes a testing stage 16. The organic electroluminescent device 3 is placed on the testing stage 16. As shown in FIG. 3, the testing stage 16 has a power supply 161, which includes a positive terminal 1611 and a negative terminal 1612. During photons, thermal or IR emission detection, the power supply 161 provides a negative bias or a low forward bias to charge the organic electroluminescent device 3. The low forward bias is charged before the organic electroluminescent device 3 is lighted on. In the current embodiment, if the defect causes short-circuited of a pixel of the organic electroluminescent device 3, photons, thermal or IR emission are generated and emitted from the periphery of the defect according to the negative bias or low forward bias. It should be noted that the data controller 14 can further generate a second control signal according to the enlarged image and the location of the defect, and the testing stage 16 acts according to the second control signal. In this embodiment, the testing state 16 is an XYZ stage.

Moreover, the detection and repair system may further include a display (not shown), which connects to the data controller 14 for showing data outputted from the data controller 14.

The present invention is described in greater detail with reference to the following embodiment.

Figure 4:
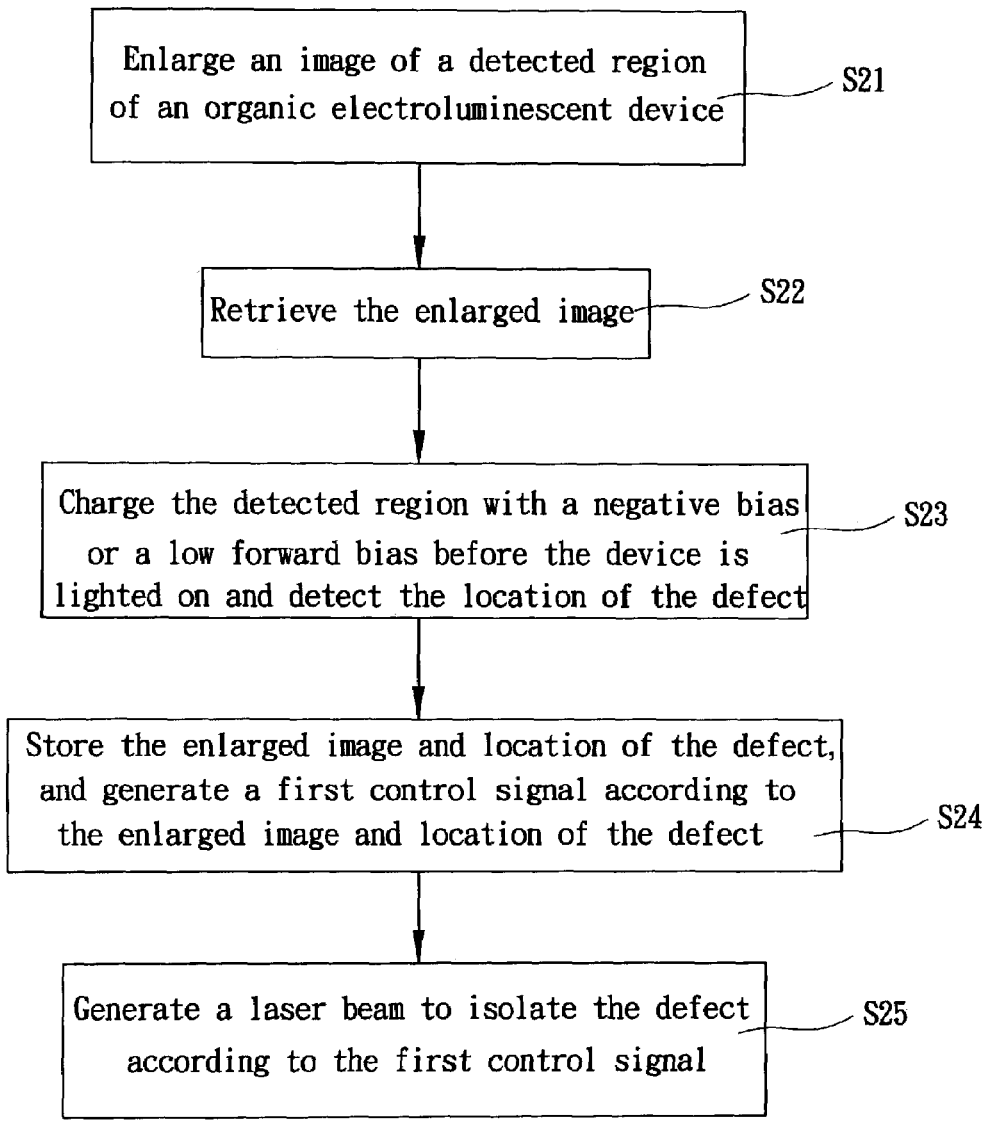
FIG. 4 is a flow chart showing a detection and repair method of the invention.

With reference to FIG. 4, a detection and repair method according to a preferred embodiment of the invention includes the following steps.

First, in step S21, the optical microscope 11 is used to enlarge the image of the detected region of the organic electroluminescent device 3. Next, in step S22, the image-retrieving device 12 is used to retrieve the enlarged image. The detected region of the organic electroluminescent device 3 is charged with a negative bias or a low forward bias before the organic electroluminescent device 3 is lighted on, in a subsequent step S23. In this step, the emission detector, such as a photon, thermal or IR emission detector, locates the defect by detecting emission such as photons, thermal or IR emission. In step S24, the data controller is then used to store the enlarged image and the location of the defect and to generate a first control signal according to the enlarged image and the location of the defect. Finally, in step S25, the laser beam generator 15 is used to generate a laser beam for isolating the defect according to the first control signal.

In the embodiment, in order to accurately radiate the laser beam to the location of the defect, the data controller 14 may further generate a second control signal according to the enlarged image and the location of the defect. Therefore, the testing stage 16, which supports the organic electroluminescent device 3, moves in accordance with the second control signal.

In summary, since an image-retrieving device and an emission detector are employed to accurately position the location of the defect, and a laser beam generator is then applied to repair the defect thus preventing short-circuited issue, it is unnecessary to transport the organic electroluminescent device when performing the disclosed detection and repairing processes. Thus simplifying redundant steps in the process, such as scanning and orientating. Furthermore, since the organic electroluminescent device is charged with a negative bias or low forward bias, the location of the defect generates emission, such as photons, thermal or IR emission, only when the defect causes short-circuited of the pixel in the organic electroluminescent device. Therefore, the defect causing short circuit can be precisely repaired, and other defects, which can be disregarded, will not be repaired. As a result, the detection and repairing processes are simplified, and the cost thereof is reduced.

Although the invention has been described with reference to specific embodiments, this description is not meant to be construed in a limiting sense. Various modifications of the disclosed embodiments, as well as alternative embodiments, will be apparent to persons skilled in the art. It is, therefore, contemplated that the appended claims will cover all modifications that fall within the true scope of the invention.

What is claimed is:

1. A detection and repair system for detection and repairing an organic electroluminescent device, comprising:
    an optical microscope for enlarging an image of a detected region located on the organic electroluminescent device;
    an image-retrieving device, which connects to the optical microscope for retrieving the image enlarged by the optical microscope;
    an emission detector, which connects to the optical microscope for detecting a location of a defect, the defect generating emission;
    a data controller, which connects respectively to the image-retrieving device and the emission detector for storing the image and the location of the defect, and generates a first control signal according to the image and the location of the defect; and
    a laser beam generator, which connects to the data controller and the optical microscope, the laser beam generator generating a laser beam according to the first control signal, the laser beam going through the optical microscope focusing on the laser beam to the location of the defect.

2. The detection and repair system of claim 1, wherein the data controller further generates a second control signal according to the image and the location of the defect.

3. The detection and repair system of claim 2, further comprising:
    a testing stage, which has a power supply for charging the organic electroluminescent device with a specific bias when the emission detector detects the location of the defect, the testing stage acting according to the second control signal.

4. The detection and repair system of claim 3, wherein the specific bias is a low forward bias charged before the device is lighted on.

5. The detection and repair system of claim 3, wherein the specific bias is a negative bias.

6. The detection and repair system of claim 3, wherein the testing stage is an XYZ stage.

7. The detection and repair system of claim 1, further comprising:
    a display, which connects to the data controller for showing data outputted from the data controller.

8. The detection and repair system of claim 1, wherein the image-retrieving device is a CCD camera.

9. The detection and repair system of claim 1, wherein the data controller is a computer.

10. The detection and repair system of claim 1, wherein the organic electroluminescent device is an organic electroluminescent panel.

11. The detection and repair system of claim 1, wherein the organic electroluminescent device is an organic electroluminescent component.

12. The detection and repair system of claim 1, wherein the emission detector is a photon detector.

13. The detection and repair system of claim 1, wherein the emission detector is a thermal emission detector.

14. The detection and repair system of claim 1, wherein the emission detector is an IR emission detector.

15. The detection and repair system of claim 1, wherein the optical microscope is a specific lens that focuses on the laser beam to the location of the defect.

* * * * *